United States Patent [19]

Brandes et al.

[11] 4,368,202

[45] Jan. 11, 1983

[54] COMBATING FUNGI WITH PYRAZOLE-SUBSTITUTED OXIMINO-CYANO-ACETAMIDE DERIVATIVES

[75] Inventors: Wilhelm Brandes, Leichlingen; Werner Daum, Krefeld, both of Fed. Rep. of Germany

[73] Assignee: Bayer Aktiengesellschaft, Leverkusen, Fed. Rep. of Germany

[21] Appl. No.: 313,110

[22] Filed: Oct. 20, 1981

[30] Foreign Application Priority Data

Oct. 7, 1980 [DE] Fed. Rep. of Germany ....... 3041998

[51] Int. Cl.³ .................... A01N 43/56; C07D 231/12
[52] U.S. Cl. ................................. 424/273 P; 548/378
[58] Field of Search ..................... 548/378; 424/273 P

[56] References Cited

U.S. PATENT DOCUMENTS 3,919,284 11/1975 Lin ....................................... 424/304
3,957,847 5/1976 Davidson ............................ 424/304

FOREIGN PATENT DOCUMENTS 23 12/1978 European Pat. Off. .
2312956 2/1973 Fed. Rep. of Germany .
2837863 3/1980 Fed. Rep. of Germany .
7808962 3/1980 Netherlands .

*Primary Examiner*—Henry R. Jiles
*Assistant Examiner*—Natalia Harkaway
*Attorney, Agent, or Firm*—Sprung, Horn, Kramer & Woods

[57] ABSTRACT

Pyrazole-substituted oximino-cyano-acetamide derivatives of the formula

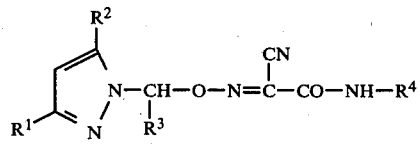

in which
  $R^1$ and $R^2$ each independently is hydrogen or alkyl with up to 3 carbon atoms,
  $R^3$ is hydrogen, alkyl with up to 6 carbon atoms or halogenoalkyl with up to 2 carbon atoms and up to 5 halogen atoms,
  $R^4$ is hydrogen or the group $CO-NH-R^5$, and
  $R^5$ is hydrogen or alkyl with up to 8 carbon atoms optionally substituted by at least one substituent selected from cyano, hydroxycarbonyl and aminocarbonyl groups and alkoxycarbonyl groups with up to 4 carbon atoms in the alkyl part, which possess fungicidal and microbicidal activity.

11 Claims, No Drawings

COMBATING FUNGI WITH PYRAZOLE-SUBSTITUTED OXIMINO-CYANO-ACETAMIDE DERIVATIVES

The present invention relates to certain new pyrazole-substituted oximino-cyano-acetamide derivatives, to a process for their preparation and to their use as fungicides.

As has already been known for a long time, zinc ethylene-1,2-bis-dithiocarbamidate and N-trichloromethylthio-tetrahydrophthalimide are used as fungicides in agriculture and in horticulture; the compounds mentioned are of great importance amongst commercial products (see R. Wegler, "Chemie der Pflanzenschutz- und Schädlingsbekämpfungsmittel" ("Chemistry of Plant Protection Agents and Agents for Combating Pests"), Volume 2, pages 65 and 108, Berlin/Heidelberg/New York (1970)). However, their action is not always satisfactory when low concentrations are applied. Furthermore, these fungicides cannot be employed curatively.

Moreover, the fungicidal action of some isonitrosocyano-acetamide derivatives is known from a number of Patent Specifications (in this context, see, for example, German Offenlegungsschrift (German Published Specification) No. 2,312,956 and U.S. Pat. Nos. 3,919,284, 3,957,847 and 4,188,401). In this case also, the activity is not reliable when small amounts are applied, and damage to plants is frequently observed at normal concentrations.

The present invention now provides, as new compounds, the pyrazole-substituted oximino-cyano-acetamide derivatives of the general formula

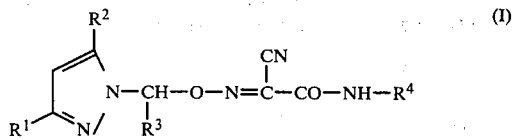

in which
R$^1$ and R$^2$, which may be identical or different, each represents hydrogen or alkyl with up to 3 carbon atoms,
R$^3$ represents hydrogen, alkyl with up to 6 carbon atoms or halogenoalkyl with up to 2 carbon atoms and up to 5 halogen atoms and R$^4$ represents hydrogen or the group CO—NH—R$^5$,
wherein
R$^5$ represents hydrogen or alkyl with up to 8 carbon atoms, it being possible for the latter to carry at least one substituent selected from cyano, hydroxycarbonyl and aminocarbonyl groups and alkoxycarbonyl groups with up to 4 carbon atoms in the alkyl part.

The compounds of the general formula (I) according to the invention can be in the form of oxime derivatives in 2 different geometric structures:

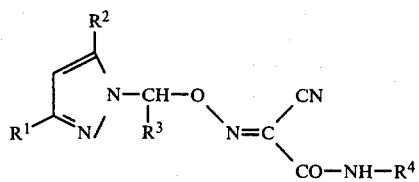

E-Derivative

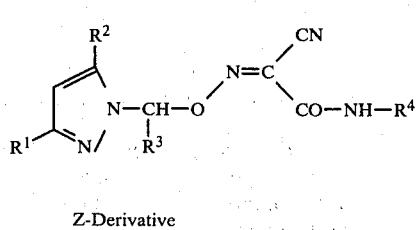

Z-Derivative

In the text which follows, the spatial structure is not given; for the purposes of the present application, the formulae given are in each case also intended to include the corresponding formula with the geometric structure E or Z.

Preferred pyrazole-substituted oximino-cyano-acetamide derivatives of the formula (I) are those in which
R$^1$ and R$^2$ represent hydrogen or methyl,
R$^3$ represents hydrogen or alkyl with 1 to 4 carbon atoms and
R$^4$ represents hydrogen or the group CO—NH—R$^5$,
wherein
R$^5$ represents hydrogen or optionally cyano-substituted alkyl with 1 to 5 carbon atoms. Particularly preferred compounds of the formula (I) are those in which
R$^1$ and R$^2$ represent hydrogen,
R$^3$ represents hydrogen, methyl, ethyl, isopropyl or sec.-butyl and
R$^4$ represents hydrogen or the group CO—NH—R$^5$,
wherein
R$^5$ represents hydrogen, methyl, ethyl, n-propyl or isopropyl.

The pyrazole-substituted oximino-cyano-acetamide derivatives of the general formula (I) have powerful fungicidal properties. They can be used protectively, curatively and even eradicatively, and they also have systemic and/or loco-systemic properties. Surprisingly, they are better tolerated by plants than the isonitrosocyanoacetamide derivatives which are known from the state of the art. Compared with the dithiocarbamidates and with N-trichloromethylthio-tetrahydrophthalimide, they have the advantage of a curative and eradicative action.

The compounds according to the invention already represent a valuable enrichment of the art because of the many possibilities of their superior biological use. An important aspect of this invention is that new active compounds which have valuable properties in practice are being made available at a time when earlier active compounds are being withdrawn from the market because of resistance phenomena.

There is thus at present and in the foreseeable future a decided need for new fungicides which can be used by themselves or, if desired, in combination with other fungicides which do not have the same action mechanism, or in an alternating combating program with these fungicides.

The invention also provides a process for the preparation of a pyrazole-substituted oximino-cyano-acetamide derivate of the formula (I), in which (a) an N-alkyl-pyrazole of the general formula

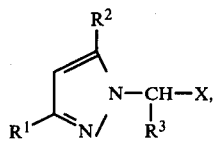

in which
 R$^1$, R$^2$ and R$^3$ have the abovementioned meanings and
 X represents a fugitive group, such as chlorine, bromine, iodine or a sulphonyloxy group,
is reacted with a 2-oximino-2-cyano-acetamide derivative of the general formula (III)

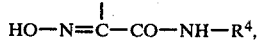

in which
 R$^4$ has the abovementioned meaning; or (b) provided a pyrazole-substituted oximino-cyano-acetamide derivative of the formula (I) in which R$^4$ represents hydrogen or the group CO—NH$_2$ is to be obtained, an N-alkylpyrazole of the formula (II) is reacted with an alkali metal salt or alkaline earth metal salt of 2-oximino-2-cyano-acetamide or of N-(2-oximino-2-cyano-acetyl)urea (thus with a compound of the general formula (III) in which R$^4$ represents hydrogen or the group CO—NH$_2$); or (c) provided a pyrazole-substituted oximino-cyano-acetamide derivative of the formula (I) in which R$^4$ represents the group CO—NH—R$^5$, in which R$^5$ has the abovementioned meanings with the exception of hydrogen or hydroxycarbonylalkyl, is to be obtained, a compound of the general formula

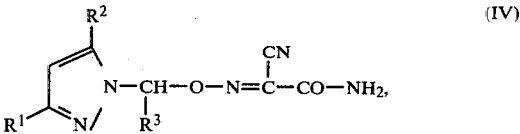

in which R$^1$, R$^2$ and R$^3$ have the abovementioned meanings, (the formula (IV) is identical to formula (I) in the case where the substituent R$^4$ in formula (I) represents hydrogen), is reacted with an isocyanate of the general formula $$OCN-R^5 \quad (V)$$

in which R$^5$ has the abovementioned meanings, with the exception of hydrogen or hydroxycarbonylalkyl, in the presence of a strong base; or (d) provided that a compound of the formula (I) in which R$^4$ represents CO—NH—R$^5$ and R$^5$ assumes the meaning of alkylcarbonyloxyalkyl is to be prepared, a carboxylic acid of the general formula

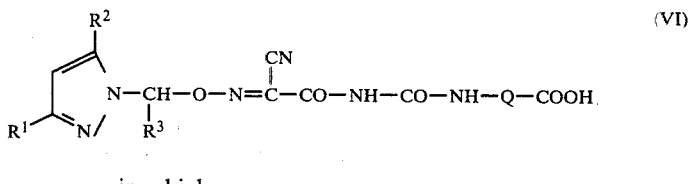

in which
 R$^1$, R$^2$ and R$^3$ have the abovementioned meanings and
 Q represents straight-chain or branched alkylene with 1 to 5 carbon atoms,
(the compounds of the formula (VI) are identical to the compounds of the formula (I) in the case where the substituent R$^4$ in formula (I) represents the group CO—NH—R$^5$ and R$^5$ denotes hydroxycarbonylalkyl), is reacted, in the form of an alkali metal salt, alkaline earth metal salt or ammonium salt thereof, with an alkylating agent of the general formula $$Y-R^6 \quad (VII),$$

in which
 R$^6$ represents alkyl with 1 to 3 carbon atoms and
 Y represents a fusitive group, such as chlorine, bromine, iodine, alkoxysulphonyloxy, alkylsulphonyloxy or arylsulphonyloxy.

If, for example, 1-chloromethyl-pyrazole hydrochloride and 1(2-oximino-2-cyano-acetyl)-3-ethyl-urea are used as starting substances according to process variant (a), and ethyl-diisopropylamine is used as the proton acceptor, the course of the reaction can be represented by the following equation:

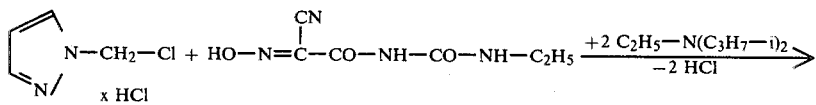

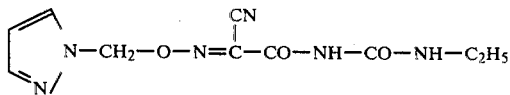

If, for example, 1-chloro-1-pyrazolyl-2-methylpropane and the potassium salt of 2-oximino-2-cyano-acetamide are used as starting substances according to process variant (b), the course of the reaction can be represented by the following equation:

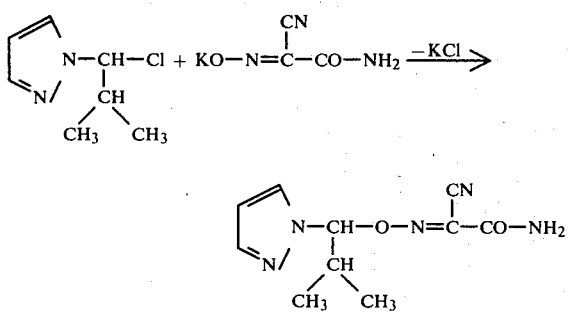

If, for example, 2-(pyrazolylmethyl-oximino)-2-cyano-acetamide, sodium hydride and n-butyl isocyanate are used as starting materials according to process variant (c), the course of the reaction can be represented by the following equation:

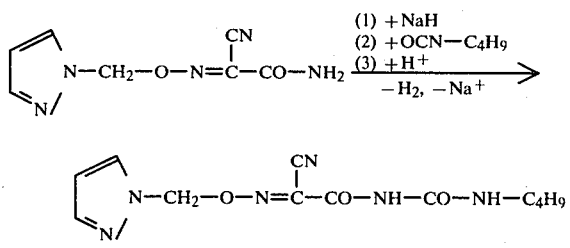

If, for example, 1-[2-(pyrazolylmethyl-oximino)-2-cyano-acetyl]-3-[5-(hydroxycarbonyl)-pentyl]-urea in the form of its sodium salt and methyl iodide are used as starting materials according to process variant (d), the course of the reaction can be represented by the following equation:

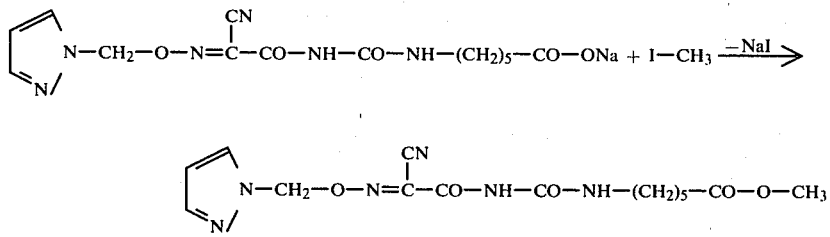

N-alkylpyrazoles of the formula (II) required as starting substances in process variants (a) or (b) are known (J. Chem. Soc. 1960, 5272-3; DE-OS (German Published Specification) Nos. 2,835,158; Chem. Ber. 85, 820 (1952)). They can be obtained, for example, by reacting an aldehyde with a pyrazole, if appropriate in an inert solvent, and then reacting the product with, for example, a thionyl halide, in which case the hydro-halides of the N-alkylpyrazoles are obtained.

The following compounds may be mentioned here as examples: 1-chloromethyl-, 1-(1-chloro-ethyl)-, 1-(1,2-dichloroethyl)-, 1-(1-chloro-2-methyl-propyl)- and 1-(1-chloromethyl-propyl)-pyrazole hydrochloride, -3- and -5-methylpyrazole hydrochloride and -3,5-dimethypyrazole hydrochloride, and 1-(1-bromoethyl)-pyrazole hydrobromide.

The 2-oximino-2-cyano-acetamide derivatives of the general formula (III) are also required for the reactions according to the invention in process variant (a) or (b). Some of the compounds are known (see Chem. Ber. 42, 738-741 (1909); Chem. Ber. 54, 1334 (1921); and U.S. Pat. No. 4,188,401). They are obtained, for example, when ethyl isocyanate is reacted with ammonia in a first stage to give N-ethyl-urea, this compound is reacted with cyanoacetic acid in the presence of acetic anhydride in a second stage and an oxime is formed from the resulting 1-ethyl-3-(2-cyanoacetyl)-urea with nitrous acid.

The isocyanates required for process variant (c) are generally known compounds; they are obtained in the customary manner, for example when primary amines are reacted with phosgene.

Compounds which may be mentioned here are: methyl, ethyl, propyl, isopropyl, butyl, sec.-butyl, ω-cyanoethyl, 1-cyano-1-methyl-ethyl, ω-cyano-propyl, ω-cyanopentyl, methoxycarbonyl-methyl, ethoxycarbonyl-methyl, propoxycarbonyl-ethyl, 1-methoxycarbonyl-1-methyl-ethyl, 1-ethoxycarbonyl-1-methyl-ethyl, ethoxycarbonyl-1-ethyl-ethyl, methoxycarbonyl-1-ethyl-ethyl, methoxycarbonyl-propyl, methoxycarbonylpentyl and isopropoxycarbonylpentyl isocyanate.

The compounds of the formula (IV) also required in process variant (c) are themselves compounds of the present invention and may be prepared by process variant (a) or (b).

The compounds of the formula (VI) required in process variant (d) are themselves compounds of the invention and may be prepared by process variant (a).

Possible diluents for process variant (a) are any of the organic solvents which are inert towards the reactants; a polar solvent is preferably used. Examples which may be mentioned here are acetonitrile, acetone, chloroform, benzonitrile, dimethyl-acetamide, dimethylformamide, dimethylsulphoxide, chlorobenzene, ethyl acetate, dioxane, methyl ethyl ketone, methylene chloride and tetrahydrofuran.

The reaction can also be carried out in mixtures of water and a water-miscible organic solvent or in heterogeneous systems consisting of water and a solvent which is water-immiscible or only partly water-miscible.

Organic bases, preferably tertiary amines, are used as acid-binding agents for the reaction according to process variant (a). Compounds which may be mentioned here are: quinoline, dimethylbenzylamine, dimethylaniline, ethyldicyclohexylamine, ethyldiisopropylamine, picoline, pyridine and triethylamine.

The reaction temperatures and the reaction time in process variant (a) are determined by the reactivity of the starting materials. In general, the reaction is carried out at between −50° and +80° C., preferably between −30° and +40° C. If water is used or co-used as the diluent, the reaction is carried out in the temperature range between the solidification point of the aqueous solution and about +60° C., preferably at from 0° to +40° C.

To carry out the process according to the invention by variant (a), the 2-oximino-2-cyano-acetamide derivative of the formula (III), dispersed or dissolved in one or more of the abovementioned diluents, is initially introduced into the reaction vessel and an equimolar amount of a tertiary amine is added, whereupon salt formation can occur. If the reaction is to be carried out with a salt of the reactive N-alkyl-pyrazole compound of the formula (II), a further equimolar amount of a tertiary amine is introduced either before the addition of the pyrazole compound or at the same time as the pyrazole compound. The reactive pyrazole compound is preferably introduced into the reaction vessel in liquid form or as a solution. The reaction mixture should be alkaline at the end of the reaction, but should then soon be rendered weakly acid.

According to a particular procedure, a small amount of an iodide is added to the mixture before the start of the reaction if a compound of the formula (II) containing iodine as a fugitive group has not itself been employed. The rate of reaction is thereby increased.

Diluents which can be used in process variant (b) are any of the solvents which are inert towards the reactants. Compounds which may be mentioned here are polar solvents, for example acetonitrile, dimethylformamide, dimethylacetamide or dimethylsulphoxide, or, if the reaction is to be carried out in suspension, aromatic hydrocarbons, for example chlorobenzene and toluene.

The reaction temperatures can likewise be varied within a substantial range in process variant (b). In general, the reaction is carried out at between −20° and +60° C., preferably between −10° and +30° C.

To carry out the process according to the invention by variant (b), an alkali metal salt or alkaline earth metal salt of the 2-oximino-2-cyano-acetamide derivative is initially introduced into the reaction vessel in an inert solvent, or the salt is produced by adding an alkali metal hydroxide or alcoholate or an alkaline earth metal hydroxide to a mixture of the 2-oximino-2-cyano-acetamide derivative and a high-boiling solvent and then carefully removing the water or distilling off the alcohol.

For reaction of the salts of the reactive N-alkyl-pyrazoles, it is expedient additionally to use an equimolar amount of a tertiary amine.

Possible diluents for process variant (c) are inert anhydrous solvents, for example ether, such as diisopropyl ether, dioxane or tetrahydrofuran.

The reaction temperatures in process variant (c) can be varied between −20° and +80° C., and the reaction is preferably carried out between +20° and 60° C.

To carry out the process according to the invention by variant (c), a 2-cyano-2-pyrazol-1-yl-methyl-oximino-acetamide derivative of the formula (IV) is converted into the corresponding alkali metal salt with sodium hydride or potassium tert.-butanolate in one of the inert solvents described in more detail above, and the alkali metal salt is then reacted with the isocyanate of the formula (V) in the given temperature range. When the reaction has ended, the mixture is rendered weakly acid in the cold with an organic carboxylic acid.

Possible diluents for process variant (d) are any of the inert solvents. Solvents which may be mentioned as preferred are acetonitrile, dioxane and ketones, for example acetone and diethyl ketone.

The reaction temperatures can be varied between −20° and +80° C. in process variant (d); the reaction is preferably carried out between +20° and 60° C.

In process variant (d), the 1-(2-cyano-2-pyrazol-1-yl-methyl-oximino)-3-(ω-carboxyalkyl)-urea derivative obtained by process variant (a) is reacted with an alkylating agent in the solvents given, after a salt has been formed with an alkali metal ion or alkaline earth metal ion or with a tertiary amine.

Depending on the conditions under which the reactions are carried out, the active compounds according to the invention precipitate as crystals, or they remain dissolved in the organic solvent and can then be separated out, after washing the solution with water, by careful concentration of the solution or by the addition of organic solvents with a low polarity, such as cyclohexane, dibutyl ether or carbon tetrachloride. If necessary, water-miscible polar solvents must be removed by evaporation in vacuo after the reaction.

If the compounds according to the invention are dissolved in a water-miscible solvent, they can also be precipitated by the addition of water. If the particular conditions of the working-up process permit, the solutions of the active compounds according to the invention or the still solvent-moist suspensions of the active compounds are rendered weakly acid. Some compounds are also readily water-soluble.

Some of the compounds according to the invention decompose at elevated temperature; in these cases, the melting points can be determined only with a low accuracy or not at all. The presence of particular structural elements can be seen from the NMR spectra. The IR spectra also exhibit characteristic absorption bands.

The active compounds according to the invention exhibit a powerful microbicidal action and can be employed in practice for combating undesired microorganism. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Oomycetes, for example against the causative organism of blight and brown rot of potato and tomato (*Phytophthora infestans*).

They exhibit a powerful curative and protective activity. Good actions can also be detected against Pyricularia and against rust fungi.

The active compounds according to the invention not only have the good properties of outstanding commercial products but moreover also have considerable advantages. These are, above all, the ability of the substances according to the invention to penetrate into the plants. They can be taken up by the surface of the seed, by the roots or by above-ground plant organs after external application. They also have the advantageous ability of acting locosystemically, that is to say of exerting a deep action in the plant tissue and of thereby eliminating fungal pathogens which have already penetrated into the tissue of the host plant.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquid which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methyl-cellulose.

In addition to the above formulation possibilities, it should be noted that the compounds according to the invention can also be formulated together with sucrose, dextrose or dextrins, with anhydrous calcium sulphate or calcium sulphate hemihydrate, or with carboxylic acids, for example fumaric acid or 4-hydroxybenzoic acid, or with weakly acidic ion exchangers.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs and azole dyestuffs and metal phthalocyanine dyestuffs, and trace nutrients such as salts of iron, manganese, boron, copper, cobalt, molybdenum and zinc.

The formulations in general contain from 0.1 to 95 percent by weight of active compound, preferably from 0.5 to 90 percent.

The active compounds according to the invention can be present in the formulations or in the various use forms as a mixture with other active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, from 1 to 0.0001% by weight, preferably from 0.5 to 0.001%.

In the treatment of seed, amounts of active compound of in general 0.001 to 50 g, preferably 0.01 to 10 g, are employed per kilogram of seed.

For the treatment of soil, active compound concentrations of in general 0.00001 to 0.1% by weight, preferably 0.0001 to 0.02%, are used at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The process of the present invention is illustrated in and by the following preparative Examples.

PREPARATIVE EXAMPLES

Example 1

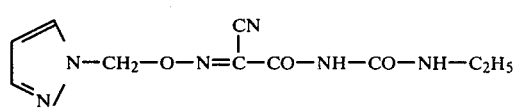

202 g (2 mols) of triethylamine were added, with slight external cooling, to 357 g (1.94 mols) of 1-(2-cyano-2-oximino-acetyl)-3-ethyl-urea, suspended in 1.5 liters of dry acetonitrile. The mixture was then cooled to about $-30°$ C. and a solution of 299 g (1.95 mols) of N-chloromethylpyrazole hydrochloride in 2 liters of dry acetonitrile was allowed to run in slowly. At the same time, about a further 178 g (1.76 mols) of triethylamine were added dropwise into the reaction vessel.

After the addition of the pyrazole component, the reaction mixture was left at a pH value of 9 for 15 minutes. Some more triethylamine had to be added, when necessary. The mixture was then rendered weakly acid with acetic acid, the cooling bath was removed and most of the acetonitrile was evaporated off in vacuo. 800 g of ice and water were added to the residue. The crystalline reaction product was separated off and washed with water until a sample no longer contained chloride. Yield after dring at 60° C./0.1 mbar: 379.6 g of 1-[2-((pyrazol-1-yl)-methoximino)-2-cyano-acetyl]-3-ethyl-urea.

The product could be further purified by being dissolved in acetone and precipitated with water. Melting point: 154° C.

Monitoring was effected by thin layer chromatography on silica gel, using a mobile phase of chloroform/methanol/toluene in a volume ratio of 1:1:1.

The following compounds of the general formula

Example 2

Phytophthora test (tomatoes)/protective

Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20° C. and at a relative atmospheric humidity of 70%. The tomato plants were then inoculated with an aqueous spore suspension of Phytophthora infestans. The plants were brought into a humidity chamber with an atmospheric humidity of 100% and a temperature of 18° to 20° C.

After 5 days the infection of the tomato plants was determined. The assessment data were converted to percent infection. 0% denoted no infection and 100% denoted that the plants were totally infected.

In this test, a clearly superior activity compared to the prior art was shown, for example, by the compounds (5) and (7).

Example 3

Phytophthora test (tomatoes)/systemic

Solvent: 4.7 parts by weight of acetone.
Dispersing agent: 0.3 part by weight of alkylaryl polyglycol ether
Water: 95 parts by weight

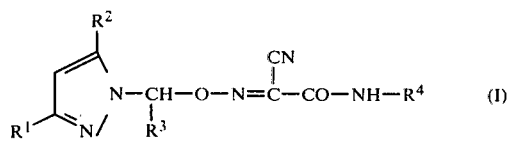

were obtained in a corresponding manner:

| Compound No. | $R^1$ | $R^2$ | $R^3$ | $R^4$ | Melting point (°C.) |
|---|---|---|---|---|---|
| 2 | H | H | H | H | 152.5 |
| 3 | H | H | H | CO—NH—$(CH_2)_5$CN | 121 |
| 4 | H | H | H | CO—$NH_2$ | 210 |
| 5 | H | H | $CH_3$ | H | 172 |
| 6 | H | H | $CH_3$ | CO—NH—$C_2H_5$ | 149 |
| 7 | H | H | $CH(CH_3)_2$ | H | 151.5 |
| 8 | H | H | $CH(CH_3)_2$ | CO—NH—$CH_3$ | 167 |
| 9 | H | H | $CH(CH_3)_2$ | CO—NH—$C_2H_5$ | 122 |
| 10 | $CH_3$ | $CH_3$ | H | CO—NH—$C_2H_5$ | 163 |
| 11 | $CH_3$ | $CH_3$ | H | CO—NH—$(CH_2)_5$—CN | 111.5 |
| 12 | $CH_3$ | $CH_3$ | H | CO—$NH_2$ | 202 |
| 13 | $CH_3$ | $CH_3$ | H | H | 142 |

The fungicidal activity of the compounds of this invention is illustrated by the following biotest Examples.

In these Examples, the compounds according to the present invention are each identified by the number (given in brackets) of the corresponding preparative Example.

The amount of the active compound required for the desired concentration of the active compound in the watering liquid was mixed with the stated amount of solvent and the concentrate was diluted with the stated amount of water which contained the stated additions.

Tomato plants grown in standard soil and having 2 to 4 foliage leaves were watered with 10 ml of the watering liquid, having the stated concentration of active compound, per 100 ml of soil.

The plants treated in this way were inoculated, after the treatment, with an aqueous spore suspension of Phytophthora infestans. The plants were brought into a humidity chamber at an atmospheric humidity of 100% and a temperature of 18° to 20° C. After 5 days, the infection of the tomato plants was determined. The assessment data were converted to percent infection. 0% denoted no infection and 100% denoted that the plants were totally infected.

In this test, a clearly superior activity compared to the prior art was shown, for example, by the compounds (2), (1), (4), (5), (7), (9), and (8).

It will be understood that the specification and examples are illustrative but not limitative of the present invention and that other embodiments within the spirit and scope of the invention will suggest themselves to those skilled in the art.

We claim:

1. A pyrazole-substituted oximino-cyano-acetamide derivative of the formula

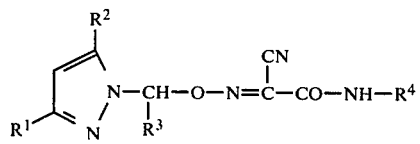

in which
R$^1$ and R$^2$ each independently is hydrogen or alkyl with up to 3 carbon atoms,
R$^3$ is hydrogen, alkyl with up to 6 carbon atoms or halogenoalkyl with up to 2 carbon atoms and up to 5 halogen atoms,
R$^4$ is hydrogen or the group CO—NH—R$^5$, and
R$^5$ is hydrogen or alkyl with up to 8 carbon atoms optionally substituted by at least one substituent selected from cyano, hydroxy-carbonyl and amino-carbonyl groups and alkoxy-carbonyl groups with up to 4 carbon atoms in the alkyl part.

2. A compound according to claim 1, in which
R$^1$ and R$^2$ each independently is hydrogen or methyl,
R$^3$ is hydrogen or alkyl with 1 to 4 carbon atoms,
R$^4$ is hydrogen or the group CO—NH—R$^5$, and
R$^5$ is hydrogen or optionally cyano-substituted alkyl with 1 to 5 carbon atoms.

3. A compound according to claim 1, in which
R$^1$ and R$^2$ are hydrogen,
R$^3$ is hydrogen, methyl, ethyl, isopropyl or sec.-butyl,
R$^4$ is hydrogen or the group CO—NH—R$^5$, and
R$^5$ is hydrogen, methyl, ethyl, n-propyl or isopropyl.

4. A compound according to claim 1, wherein such compound is 2-((pyrazol-1-yl)-methoximino)-2-cyano-acetamide of the formula

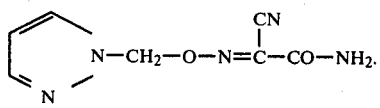

5. A compound according to claim 1, wherein such compound is 2-(1-(pyrazol-1-yl)-ethoximino)-2-cyano-acetamide of the formula

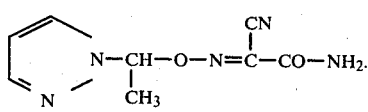

6. A compound according to claim 1, wherein such compound is 2-(2-methyl-1-(pyrazol-1-yl)-propoximino)-2-cyano-acetamide of the formula

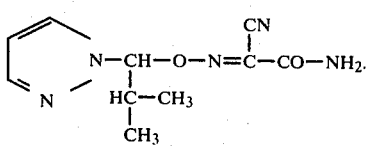

7. A compound according to claim 1, wherein such compound is 2-(2-methyl-1-(pyrazol-1-yl)-propoximino)-2-cyano-acetyl-3-methyl-urea of the formula

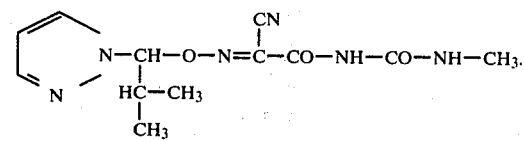

8. A compound according to claim 1, wherein such compound is 2-(2-methyl-1-(pyrazol-1-yl)-propoximino)-2-cyano-acetyl-3-ethyl-urea of the formula

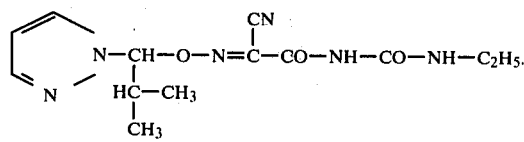

9. A fungicidal or microbicidal composition comprising a fungicidally or microbicidally effective amount of a compound according to claim 1 in admixture with a diluent.

10. A method of combating fungi or microbes comprising applying to the fungi or microbes, or to a habitat thereof, a fungicidally or microbicidally effective amount of a compound according to claim 1.

11. A method according to claim 10, in which said compound is
2-((pyrazol-1-yl)-methoximino)-2-cyano-acetamide,
2-(1-pyrazol-1-yl)-ethoximino)-2-cyano-acetamide,
2-(2-methyl-1-(pyrazol-1-yl)-propoximino)-2-cyano-acetamide,
2-(2-methyl-1-(pyrazol-1-yl)-propoximino)-2-cyano-acetyl-3-methyl-urea or
2-(2-methyl-1-(pyrazol-1-yl)-propoximino)-2-cyano-acetyl-3-ethyl urea.

* * * * *

UNITED STATES PATENT AND TRADEMARK OFFICE
CERTIFICATE OF CORRECTION

PATENT NO. : 4,368,202
DATED : January 11, 1983
INVENTOR(S) : Wilhelm Brandes et al It is certified that error appears in the above—identified patent and that said Letters Patent is hereby corrected as shown below:

On the title page Item [30] Foreign Application Priority Data    Delete "Oct. 7, 1980" and insert --Nov. 7, 1980--

Col. 11, line 28    Delete "dring" and insert --drying--

Signed and Sealed this

Fifth Day of April 1983

[SEAL]

Attest:

GERALD J. MOSSINGHOFF

Attesting Officer    Commissioner of Patents and Trademarks